US009116526B2

(12) United States Patent
Hashimoto et al.

(10) Patent No.: US 9,116,526 B2
(45) Date of Patent: Aug. 25, 2015

(54) GAS CONCENTRATION CONTROLLER SYSTEM

(75) Inventors: Yuichiro Hashimoto, Kyoto (JP); Junichi Miyaji, Kyoto (JP)

(73) Assignee: HORIBA STEC, Co., Ltd., Kyoto-shi (JP)

( * ) Notice: Subject to any disclaimer, the term of this patent is extended or adjusted under 35 U.S.C. 154(b) by 357 days.

(21) Appl. No.: 13/327,678

(22) Filed: Dec. 15, 2011

(65) Prior Publication Data

US 2012/0152364 A1    Jun. 21, 2012

(30) Foreign Application Priority Data

Dec. 17, 2010   (JP) .................................. 2010-282092

(51) Int. Cl.
*F17D 3/00* (2006.01)
*G05D 11/13* (2006.01)
*G01N 33/00* (2006.01)

(52) U.S. Cl.
CPC .......... *G05D 11/132* (2013.01); *G01N 33/0006* (2013.01)
USPC ................. 137/599.07; 137/599.04; 137/597; 137/486; 137/487.5

(58) Field of Classification Search
USPC ............. 137/599.01, 599.03, 599.04, 599.07, 137/597, 487.5, 486
See application file for complete search history.

(56) References Cited

U.S. PATENT DOCUMENTS 5,241,987 A *   9/1993  Ohmi et al. ................... 137/597
5,358,874 A    10/1994  Tsurumi
5,661,225 A    8/1997  Ridgeway et al.
5,744,695 A *   4/1998  Forbes ........................... 73/1.35
7,137,400 B2 *  11/2006  Bevers et al. ...................... 137/1
2004/0056044 A1   3/2004  Hirahara et al.
2005/0014366 A1*  1/2005  Fujiwara et al. .............. 438/681

(Continued)

FOREIGN PATENT DOCUMENTS

CN   2499819 Y   7/2002
CN   1493716 A   5/2004

(Continued)

OTHER PUBLICATIONS

European Patent Office, Extended European Search Report of EP11009738-3, Mar. 20, 2013, Germany, 6 pages.

(Continued)

*Primary Examiner* — John Rivell
*Assistant Examiner* — Ian Paquette
(74) *Attorney, Agent, or Firm* — Alleman Hall McCoy Russell & Tuttle LLP

(57) ABSTRACT

The present invention is one that prevents standard gas from remaining in a standard gas line to prevent a concentration of standard gas from being reduced due to adsorption, modification, or the like, and has: a diluent gas line provided with a diluent gas flow rate controlling mechanism; a standard gas line provided with a standard gas flow rate controlling mechanism; an output gas line joined by the diluent gas line and standard gas line and outputs the standard gas having a predetermined concentration; an exhaust gas line connected to an upstream side of the standard gas flow rate controlling mechanism in the standard gas line and provided with an on/off valve and a flow rate control part; and a control part that, depending on a flow rate of the standard gas flowing through the standard gas line or the type of the standard gas, switches on/off the on/off valve.

6 Claims, 5 Drawing Sheets

(56) References Cited

U.S. PATENT DOCUMENTS

2006/0254656 A1 11/2006 Malczewski et al.
2008/0202610 A1* 8/2008 Gold et al. .................... 137/597
2012/0298221 A1* 11/2012 Takeuchi et al. ............. 137/497

FOREIGN PATENT DOCUMENTS

| | | |
|---|---|---|
| CN | 101218014 A | 7/2008 |
| JP | 61116638 A | 6/1986 |
| JP | 04233725 A | 8/1992 |
| JP | 10104130 | 4/1998 |

OTHER PUBLICATIONS

Chinese Patent Office, First Office Action in Application No. 201110407489, Sep. 25, 2014, China, 15 pages.

\* cited by examiner

GAS CONCENTRATION CONTROLLER SYSTEM

TECHNICAL FIELD

The present invention relates to a gas concentration controller system that generates calibration standard gas used to calibrate a gas analyzer such as an exhaust gas analyzing system and mixes first gas such as diluent gas and second gas such as standard gas at a predetermined ratio to produce mixed gas having a predetermined concentration.

BACKGROUND ART

In order to calibrate a gas analyzer such as an exhaust gas analyzing system, it is necessary to supply standard gas having a predetermined concentration to the gas analyzer. Also, as a system that produces the standard gas having a predetermined concentration, as disclosed in Patent Literature 1 or the like, there is a standard gas concentration controller system that has: a diluent gas line that is supplied with diluent gas; a standard gas line that is supplied with standard gas having high concentration; and an output gas line that is joined by the diluent and standard gas lines and outputs diluted standard gas having a predetermined concentration to a gas analyzer. In the standard gas concentration controller system, the diluent line is provided with a mass flow controller for controlling a flow rate of the diluent gas, and the standard gas line is provided with a mass flow controller for controlling a flow rate of the standard gas.

However, in the case of using the standard gas concentration controller system having the above configuration to produce the low concentration standard gas, it is necessary to control the flow rate of the standard gas flowing through the standard gas line to a low flow rate with use of the mass flow controller provided in the standard gas line. If doing so, on an upstream side of the mass flow controller in the standard gas line, the standard gas remains. If the standard gas has adsorptive property, there occurs a problem that the standard gas adsorbs onto an inner surface of a pipe constituting the standard gas line. If the standard gas adsorbs onto the inner surface of the pipe as described, a concentration of the standard gas supplied to the output gas line is reduced, and consequently, a concentration of the produced standard gas also becomes lower than the predetermined concentration. Further, there occurs a problem that the gas analyzer calibrated with use of the standard gas is also inaccurately calibrated.

Also, if the pipe constituting the standard gas line is one having gas permeability, such as a Teflon tube, a gas component (such as oxygen) in outside air permeates the standard gas line. If the standard gas is one having a reactive property with a permeating gas component (such as oxygen) and, such as NO gas, there occurs a problem that the standard gas reacts with oxygen to reduce the concentration of the standard gas. If so, the concentration of the standard gas supplied to the output gas line is reduced, and a concentration of the produced standard gas also becomes lower than the predetermined concentration. This causes a problem that the gas analyzer is also inaccurately calibrated.

CITATION LIST

Patent Literature

Patent literature 1: JPA Heisei 10-104130

SUMMARY OF INVENTION

Technical Problem

Therefore, the present invention is made to solve the above problems, and has a main object to prevent gas from remaining in a gas line to prevent a concentration of the gas from being reduced due to adsorption, modification, or the like, of the gas.

Solution to Problem

That is, a gas concentration controller system according to the present invention is one configured to mix a first gas and a second gas at a predetermined ratio to produce mixed gas having a predetermined concentration, and provided with: a first gas line that is provided with a first gas flow rate controlling mechanism for controlling a flow rate of the first gas; a second gas line that is provided with a second gas flow rate controlling mechanism for controlling a flow rate of the second gas; an output gas line that is joined by the first gas line and the second gas line and is configured to output the mixed gas having the predetermined concentration; an exhaust gas line that is connected to an upstream side of the second gas flow rate controlling mechanism in the second gas line and provided with an on/off valve and a flow rate control part configured to flow the second gas having a constant flow rate; and a control part configured to, depending on the flow rate of the second gas flowing through the second gas line or the type of the second gas, switch on/off the on/off valve provided in the exhaust gas line.

If so, the exhaust gas line is provided on the upstream side of the flow rate controlling mechanism of the second gas line, and the on/off valve provided in the exhaust gas line is opened/closed depending on the gas flow rate or the type of the gas, so that the second gas can be prevented from remaining in the second gas line. Accordingly, a problem caused by the remains of the second gas due to adsorption, modification, or the like can be reduced to control the concentration of the produced mixed gas to a desired concentration. This enables a gas analyzer to be accurately calibrated. Also, the flow rate of the second gas flowing through the exhaust gas line is made constant by the flow rate control part, and therefore while, limiting the flow rate of the second gas flowing from the second gas line to the exhaust gas line to ensure the second gas flowing through the flow rate controlling mechanism of the second gas line, the remains of the second gas on the upstream side of the flow rate controlling mechanism can be solved.

In order to make an effect of the present invention more pronounced, preferably, the first gas is diluent gas, and the second gas is standard gas.

In order to, along with a specific embodiment of the second gas line, prevent the second gas from remaining in the embodiment, preferably, the second gas line has: a plurality of branch lines that are respectively provided with the second gas flow rate controlling mechanisms; and a line switching mechanism configured to select, from the branch lines, a branch line through which the second gas flows, flow rate control ranges of the second gas flow rate control mechanisms provided in the respective branch lines are configured to be mutually different, and the exhaust gas line is connected to, among the plurality of branch lines, a branch line that is provided with a second gas flow rate controlling mechanism having a low flow rate range. Among the second gas flow rate control mechanisms provided in the respective branch lines, in a branch line provided with a second gas flow rate controlling mechanism having a high flow rate range, the second gas is unlikely to remain, and therefore it is not indispensable to provide the exhaust gas line. On the other hand, in the branch line provided with the second gas flow rate controlling mechanism having the low flow rate range, the second gas is likely to remain, and therefore the remains can be solved by employing the above configuration.

As a method for the control part to switch the on/off valve, the case where a target flow rate value inputted to the second gas flow rate controlling mechanism is equal to or less than a predetermined value or other case is possible. In this case, in order to simplify control of the on/off valve by the control part, preferably, in the case where, among the plurality of branch lines, the branch line that is provided with the second gas flow rate controlling mechanism having the low flow rate range is selected, the control part is configured to open the on/off valve provided in the exhaust gas line.

Also, a gas concentration controller program according to the present invention is one that is used for a gas concentration controller system configured to mix a first gas and a second gas at a predetermined ratio to produce mixed gas having a predetermined concentration and is provided with: a first gas line that is provided with a first gas flow rate controlling mechanism for controlling a flow rate of the first gas; a second gas line that is provided with a second gas flow rate controlling mechanism for controlling a flow rate of the second gas; an output gas line that is joined by the first gas line and the second gas line and configured to output the mixed gas having the predetermined concentration; and an exhaust gas line that is connected to an upstream side of the second gas flow rate controlling mechanism in the second gas line and provided with an on/off valve and a flow rate control part configured to flow the second gas having a constant flow rate, and instruct a computer to fulfill a function as a control part configured to, depending on the flow rate of the second gas flowing through the second gas line or the type of the second gas, switch on/off the on/off valve provided in the exhaust gas line.

Further, a gas concentration controller method according to the present invention is one using a gas concentration controller system configured to mix a first gas and a second gas at a predetermined ratio to produce mixed gas having a predetermined concentration and is provided with: a first gas line that is provided with a first gas flow rate controlling mechanism for controlling a flow rate of the first gas; a second gas line that is provided with a second gas flow rate controlling mechanism for controlling a flow rate of the second gas; an output gas line that is joined by the first gas line and the second gas line and configured to output the mixed gas having the predetermined concentration; and an exhaust gas line that is connected to an upstream side of the second gas flow rate controlling mechanism in the second gas line and provided with an on/off valve and a flow rate control part configured to flow the second gas having a constant flow rate, and, depending on the flow rate of the second gas flowing through the second gas line or the type of the second gas, configured to switch on/off the on/off valve provided in the exhaust gas line.

Advantageous Effects of Invention

According to the present invention configured as described, the standard gas can be prevented from remaining in the standard gas line to prevent a concentration of the standard gas from being reduced due to adsorption, modification, or the like, of the standard gas.

DETAILED DESCRIPTION OF THE EMBODIMENTS

Figure 1:
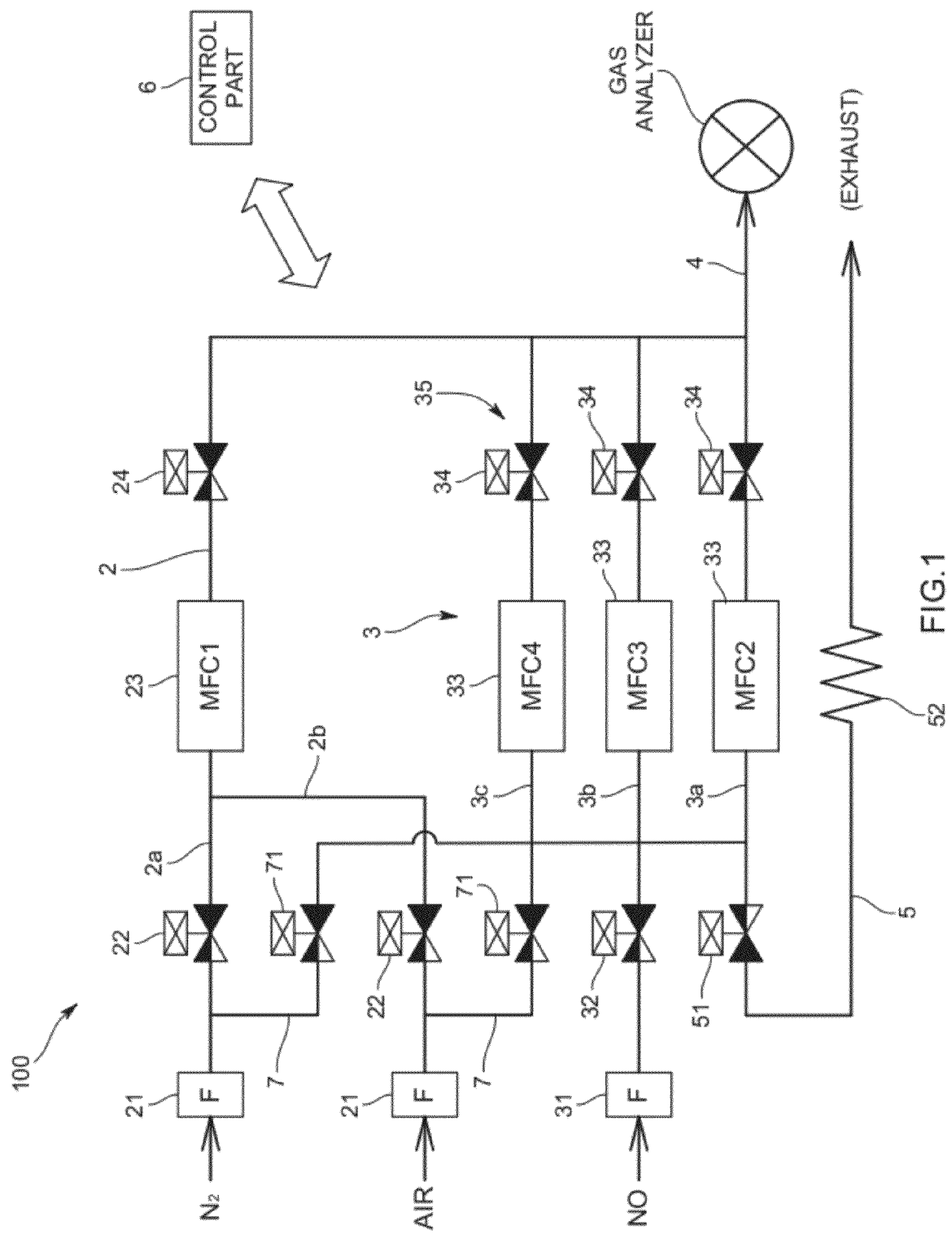
FIG. 1 is a schematic configuration diagram of a standard gas concentration controller system according to one embodiment of the present invention.

In the following, one embodiment of a standard gas concentration controller system according to the present invention is described referring to the drawings.

<System Configuration>

A standard gas concentration controller system 100 according to the present embodiment is one that produces calibration standard gas for calibrating an exhaust gas analyzing system that analyzes, for example, concentrations of components, and the like, in exhaust gas from an engine of a vehicle, such as NOx, and mixes diluent gas serving as first gas and standard gas serving as second gas at a predetermined ratio to produce standard gas (mixed gas) having a predetermined concentration. For example, the standard gas concentration controller system 100 is configured to be able to appropriately set 0% to 100% as a dilution ratio (division ratio="standard gas flow rate"/"diluent gas flow rate").

Specifically, this system is, as illustrated in FIG. 1, provided with: a diluent gas line 2 that is provided with a diluent gas flow rate controlling mechanism 23 for controlling a flow rate of the diluent gas; a standard gas line 3 that is provided with a standard gas flow rate controlling mechanism 33 for controlling a flow rate of the standard gas; an output gas line 4 that is joined by the diluent and standard gas lines 2 and 3 and outputs the standard gas having the predetermined concentration; an exhaust gas line 5 that discharges standard gas having a predetermined flow rate from the standard gas line 3; and a control part 6 that controls the diluent gas flow rate controlling mechanism 23, the standard gas flow rate controlling mechanism 33, and the like. In addition, an outlet of the output gas line 4 is connected to a gas analyzer.

The diluent gas line 2 is connected with diluent gas sources (not illustrated) on its upstream side, and, through dust filters 21, provided with upstream side on/off valves 22, the diluent gas flow rate controlling mechanism 23, and a downstream side on/off valve 24 in that order. The diluent gas flow rate controlling mechanism 23 is a mass flow controller (MFC1) that has: a thermal or differential pressure type diluent gas flow rate measurement part; and a diluent gas flow rate control valve that is controlled by the control part 6 on the basis of a flow rate measurement signal from the diluent gas flow rate measurement part.

The present embodiment is configured to be able to switch between nitrogen gas and air to supply either one of them as the diluent gas. Specifically, on an upstream side of the diluent gas flow rate controlling mechanism 23, a nitrogen gas supply line 2a and an air supply line 2b are provided, and each of the supply lines 2a and 2b is provided with a dust filter 21 and upstream side on/off valve 22. The present embodiment is configured such that the control part 6 switches on/off the upstream side on/off valve 22 provided in each of the supply lines 2a and 2b to thereby switch between the diluent gas types to be supplied to the diluent gas flow rate controlling mechanism 23. In addition, the nitrogen gas supply line 2a and the air supply line 2b are connected to the standard gas line 3 through connecting lines 7, and configured to be able to purge the standard gas line 3. Further, the connecting lines 7 are respectively provided with on/off valves 71.

The standard gas line 3 is connected with a standard gas source (not illustrated) on its upstream side, and, through a dust filter 31, provided with an upstream side on/off valve 32, the standard gas flow rate controlling mechanism 33, and a downstream side on/off valve 34 in that order. In the present embodiment, the case where NO gas is used as the standard gas is described. NO gas is characterized by easily adsorbing onto an inner surface of a line pipe, and also easily reacting with another gas component (such as oxygen) to be modified. Besides, depending on a component to be measured by the gas analyzer, the standard gas can be appropriately selected.

Specifically, the standard gas line 3 has: a plurality of branch lines 3a, 3b, and 3c that respectively have different standard gas flow rate control ranges; and a line switching mechanism 35 that selects, from the branch lines 3a, 3b, and 3c, a branch line through which the standard gas flows. The standard gas line 3 is branched into the plurality of lines (in the present embodiment, three lines) on a downstream side of the upstream side on/off valve 32, and each of the branch lines 3a, 3b, and 3c is provided with the standard gas flow rate controlling mechanism 33. In addition, in the standard gas line 3, a Teflon tube (not illustrated) is used to make a connection to the standard gas source. If the Teflon tube is used under high pressure, oxygen in outside air permeates the tube. This causes the standard gas (NO gas) inside the Teflon tube to react with the permeated oxygen to produce $NO_2$.

The standard gas flow rate controlling mechanism 33 of the present embodiment is a mass flow controller (MFC) that has: a thermal or differential pressure type standard gas flow rate measurement part; and a standard gas flow rate control valve that is controlled by the control part 6 on the basis of a flow rate measurement signal from the standard gas flow rate measurement part. The standard gas flow rate controlling mechanisms 33 provided in the respective branch lines 3a, 3b, and 3c are configured to have mutually different flow rate control ranges. Specifically, a flow rate control range of the standard gas flow rate controlling mechanism 33 (MFC2) provided in the first branch line 3a is 2% to 100% of a full scale (e.g., a full scale of 5 LM (N2-equivalent flow rate)); a flow rate control range of the standard gas flow rate controlling mechanism 33 (MFC3) provided in the second branch line 3b is 2% to 100% of a full scale (e.g., a full scale of 500 ccm (N2-equivalent flow rate)); and a flow rate control range of the standard gas flow rate controlling mechanism 33 (MFC4) provided in the third branch line 3a is 2% to 100% of a full scale (e.g., a full scale of 50 ccm (N2-equivalent flow rate)). That is, the standard gas flow rate controlling mechanisms 33 (MFC2 to MFC4) provided in the respective branch lines 3a, 3b, and 3c are configured to have mutually different full scales.

The line switching mechanism 35 is configured to have the downstream side on/off valves 34 that are provided on downstream sides of the standard gas flow rate controlling mechanisms 33 of the respective branch lines 3a, 3b, and 3c. An on/off control signal for each of the downstream side on/off valves 34 is inputted by the control part 6.

The exhaust gas line 5 is connected to upstream sides of the standard gas flow rate controlling mechanisms 33 of the standard gas line 3, and provided with an on/off valve 51 and a flow rate control part 52 that flows the standard gas having a constant flow rate. Specifically, the exhaust gas line 5 is connected on the upstream sides of the standard gas flow rate controlling mechanisms 33 in the respective branch lines 3a, 3b, and 3c. Also, the flow rate control part 52 is configured with use of a throttle mechanism such as a capillary tube, orifice, or Venturi tube. The present embodiment is configured to use a capillary tube that meets a constant flow rate (e.g., 300 ccm) in the case of a constant primary pressure (e.g., 100 kPa). Besides, as the flow rate control part 52, a mass flow controller may be used.

The control part 6 is one that controls the upstream side on/off valves 21 and 31, downstream side on/off valves 24 and 34, the diluent gas flow rate controlling mechanism 23, standard gas flow rate controlling mechanisms 33, the on/off valve 51, and the like provided in the respective lines 2, 3, and 5 to set a flow rate of the diluent gas flowing through the diluent gas line 2 and a flow rate of the standard gas flowing through the standard gas line 3, and thereby sets a concentration of the calibration standard gas outputted from the output gas line 4. The control part 6 incorporates a circuit part (not illustrated) mounted with a CPU, an internal memory, and the like, and according to a program stored in the internal memory, actuates the CPU and peripheral devices. In addition, each of the on/off valves provided in the respective lines 2, 3, and 5 is a solenoid valve.

The control part 6 switches on/off the on/off valve 51 provided in the exhaust gas line 5 depending on the flow rate of the standard gas flowing through the standard gas line 3. Specifically, in the case where the flow rate of the standard gas flowing through the standard gas line 3 is equal to or less than a predetermined value, that is, in the case where a target flow rate value inputted to the standard gas flow rate controlling mechanism 33 (flow rate control valve) provided in the standard gas line 3 is equal to or less than the predetermined value, the control part 6 outputs an open control signal to the on/off valve 51 provided in the exhaust gas line 5 to cause part of the standard gas to flow through the exhaust gas line 5.

More specifically, in the case where a branch line provided with a standard gas flow rate controlling mechanism 33 having a low flow rate range (e.g., the second or third branch line 3b or 3c) is selected among the plurality of branch lines 3a, 3b, and 3c, the control part 6 opens the on/off valve 51 provided in the exhaust gas line 5. That is, the control part 6 outputs on/off control signals to the downstream side on/off valves 34 constituting the line switching mechanism 35, and in the case where the second or third branch line 3b or 3c is selected, outputs the open control signal to the on/off valve 51 of the exhaust gas line 5. Based on this, even in the case where the flow rate of the standard gas flowing through the standard gas line 3 is within the low flow rate range, the standard gas flows through the exhaust gas line 5, so that the standard gas can be constantly brought into a dynamic state (state of being unlikely to remain) on the upstream side of the standard gas flow rate controlling mechanism 33 in the standard gas line 3 to thereby reduce the problem of adsorption, modification, or the like of the standard gas. Note that the low flow rate range refers to a range where the flow rate of the standard gas flowing through the standard gas line 3 is equal to or less than 10% of a flow rate of the diluted standard gas flowing through the output gas line 4. In this case, the flow rate of the diluted standard gas flowing through the output gas line 4 may have a value equivalent to an actual gas flow rate.

Figure 2:
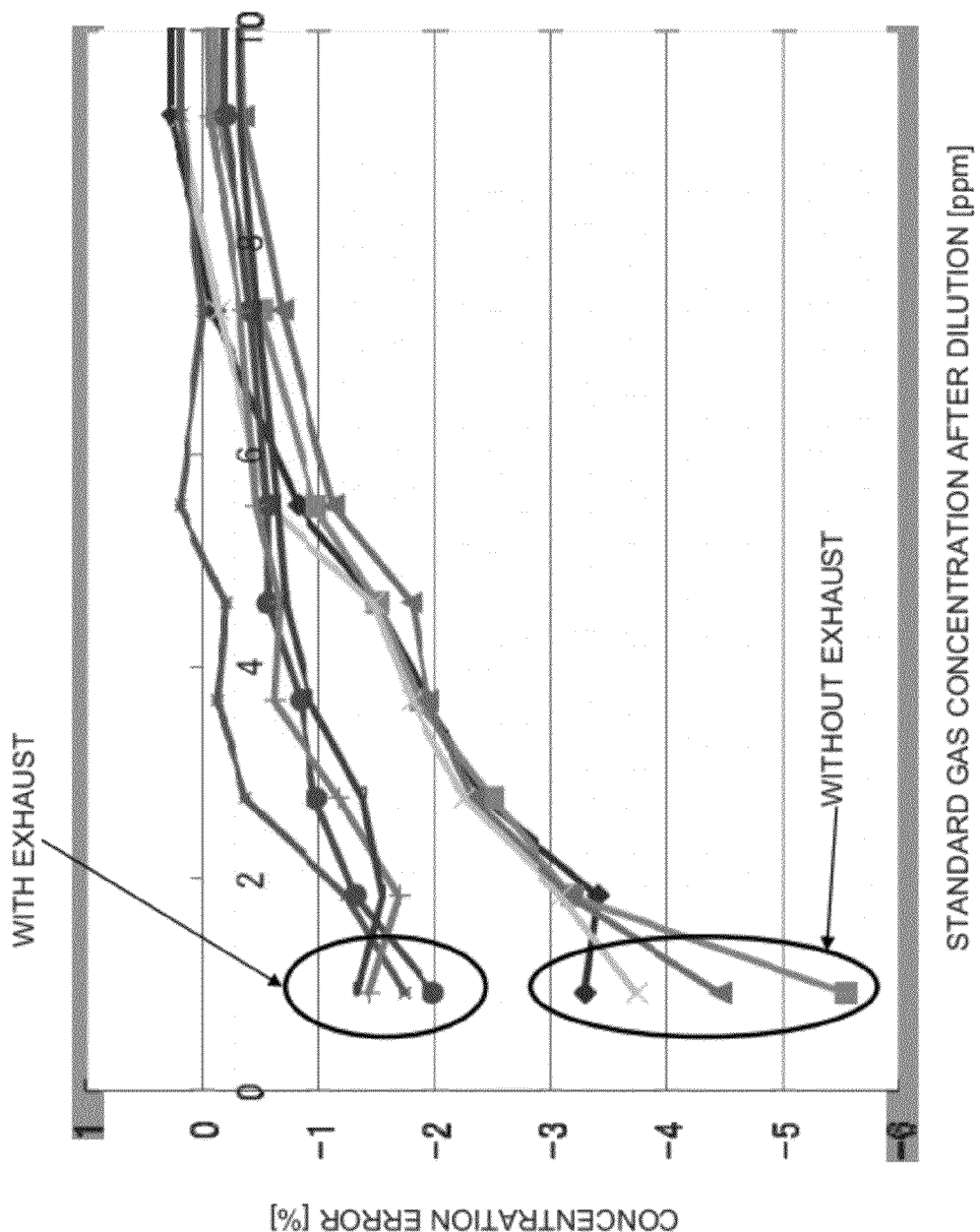
FIG. 2 is an experimental result illustrating errors of a standard gas concentration for the case of discharge through an exhaust gas line and for the case of non-discharge.

Next, errors of measured values with respect to theoretical values of a standard gas concentration in the case of using the exhaust gas line 5 to discharge part of the standard gas and in the case of not discharging the standard gas are illustrated in FIG. 2. Note that in this experiment, the flow rate of the standard gas flowing through the exhaust gas line 5 was set to 300 ccm. The horizontal axis represents the standard gas concentration [ppm] after dilution, and the vertical axis represents the concentration error [%]. As can be seen from FIG. 2, as the standard gas concentration is decreased, the concentration error increases, but an increase in concentration error is small in the discharge case as compared with the non-discharge case. It turns out from this result that by discharging the part of the standard gas through the exhaust gas line 5, the standard gas is relieved from remaining on the upstream side of the standard gas flow rate controlling mechanism 33 in the standard gas line 3.

Figure 3:
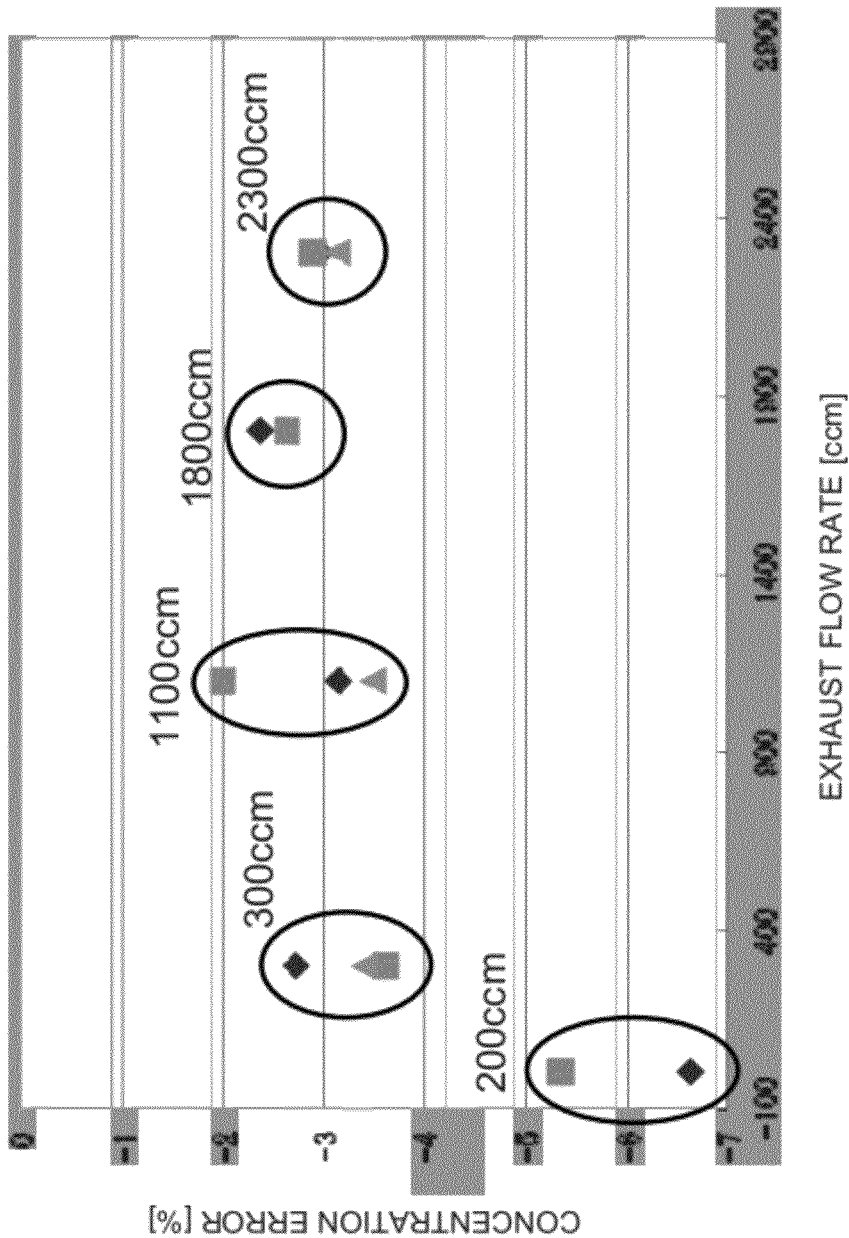
FIG. 3 is an experimental result illustrating errors of the standard gas concentration depending on a discharge flow rate through the exhaust gas line.

Next errors of the standard gas concentration depending on a discharge flow rate through the exhaust gas line 5 are illustrated in FIG. 3. Note that in this experiment, the dilution ratio was set to 0.2%. The horizontal axis represents the discharge flow rate [ccm] and the vertical axis represents the concentration error [%] at the dilution ratio of 0.2%. As can be seen from FIG. 3, in the case where the discharge flow rate through the exhaust gas line 5 is 200 ccm, the concentration error is large as compared with the case where the discharge flow rate is 300 ccm or more. It turns out from this result that by setting the discharge flow rate to 300 ccm or more, the standard gas is relieved from remaining on the upstream side of the standard gas flow rate controlling mechanism 33 in the standard gas line 3. In addition, in light of running cost of the standard gas, the discharge flow rate is preferably set to 300 ccm.

Figure 4:
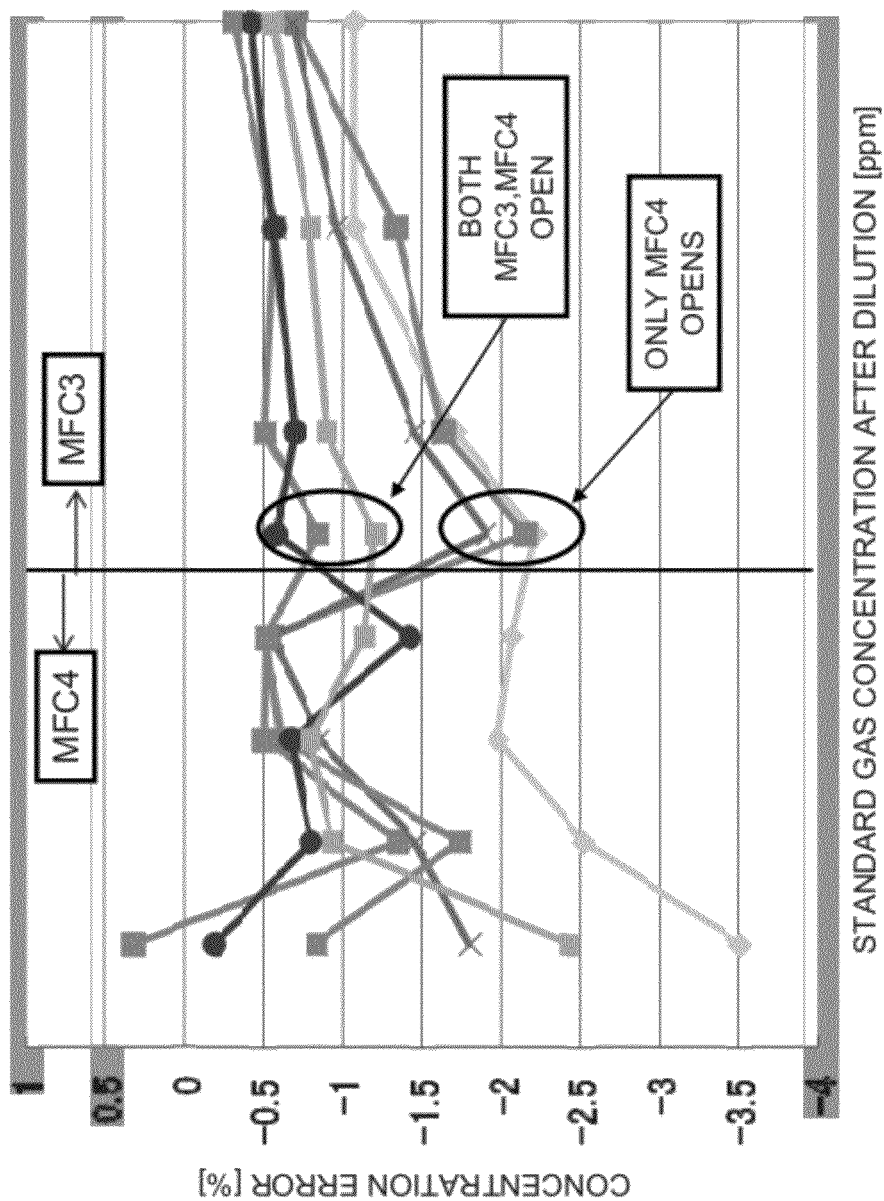
FIG. 4 is an experimental result illustrating errors of the standard gas concentration depending on a measurement control range.

Next, errors of the standard gas concentration depending on a measurement control range are illustrated in FIG. 4. FIG. 4 illustrates errors of the standard gas concentration for the case of discharge through the exhaust gas line 5 in the case of flowing the standard gas through both of the second and third branch lines 3b and 3c and for the case of discharge through the exhaust gas line 5 in the case of flowing the standard gas only through the third branch line 3c. The horizontal line represents the standard gas concentration after dilution [ppm] and vertical axis represents the concentration error [%]. As can be seen from FIG. 4, if the discharge is performed in the case of flowing the standard gas only through the third branch line 3c, at the time of switching from the second branch line 3b to the third branch line 3c, the concentration error becomes larger before the discharge. Note that in FIG. 4, three points indicated by "Both MFC3 and MFC4 open" represent concentration errors for the case of discharge in the case of flowing the standard gas through both of the second and third branch lines 3b and 3c. Also, three points indicated by "Only MFC4 opens" represent concentration errors for the case of discharge in the case of flowing the standard gas only through the third branch line 3c. It turns out from this result that the discharge is preferably performed in the case of flowing the standard gas through both of the second and third branch lines 3b and 3c.

Effects of the Present Embodiment

According to the standard gas concentration controller system 100 of the present embodiment configured as described, the exhaust gas line 5 is provided on the upstream side of the standard gas flow rate controlling mechanism 33 of the standard gas line 3, and the on/off valve 51 provided in the exhaust gas line 5 is opened/closed depending on the gas flow rate, so that the standard gas can be prevented from remaining in the standard gas line 3. Accordingly, a problem caused by the remains of the standard gas due to adsorption, modification, or the like can be reduced to control a concentration of the produced standard gas to a desired concentration. This enables the gas analyzer to be accurately calibrated.

Also, a flow rate of the standard gas flowing through the exhaust gas line 5 is made constant by the flow rate control part 52, and therefore while limiting the flow rate of the standard gas flowing from the standard gas line 3 to the exhaust gas line 5 to ensure the standard gas flowing through the standard gas flow rate controlling mechanism 33 of the standard gas line 3, the remains of the standard gas on the upstream side of the standard gas flow rate controlling mechanism 33 can be solved.

Other Variations

Note that the present invention is not limited to the above-described embodiment.

Figure 5:
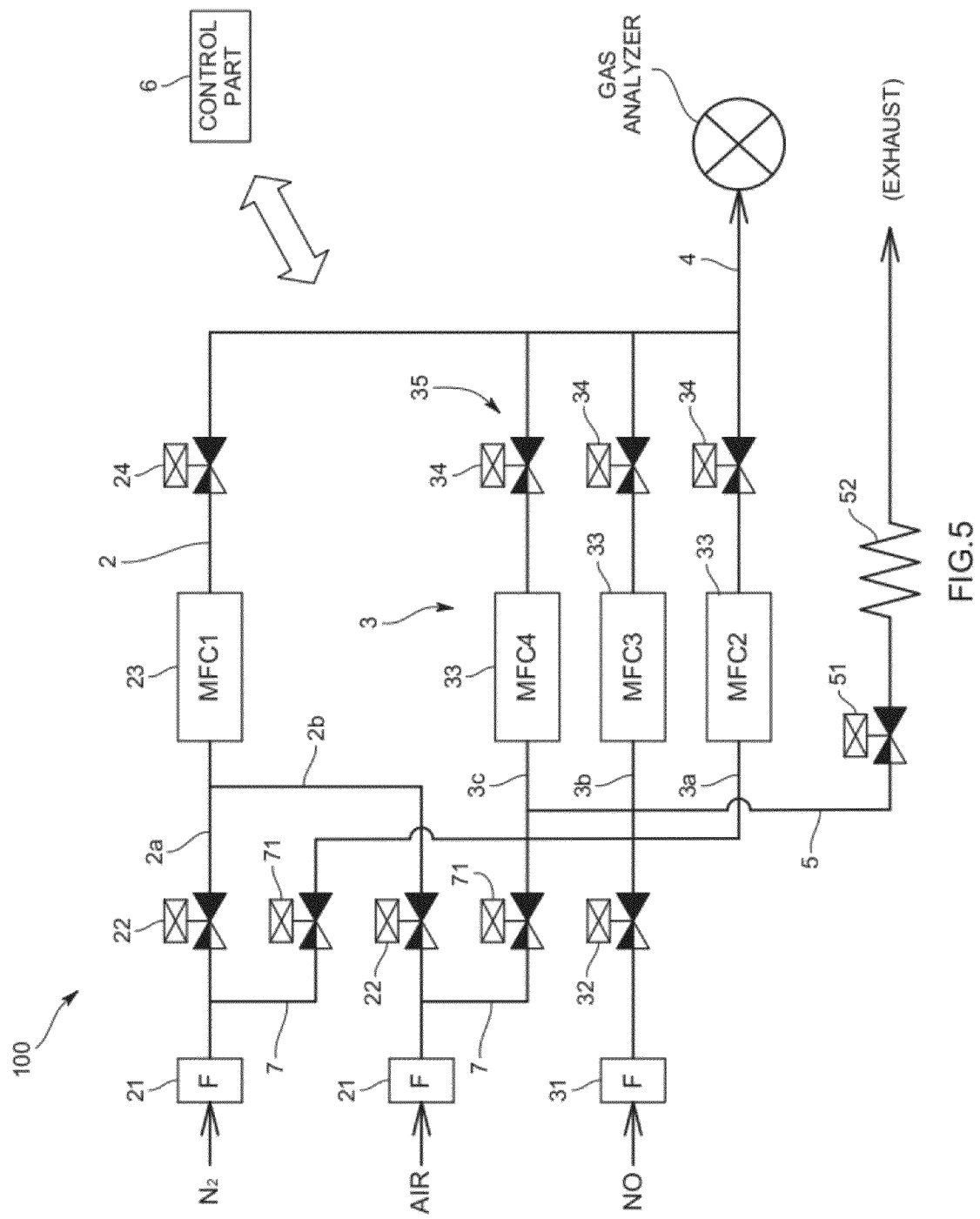
FIG. 5 is a schematic configuration diagram of a standard gas concentration controller system according to a variation embodiment.

For example, the above-described embodiment is configured such that the exhaust gas line 5 is connected to all of the branch lines; however, as illustrated in FIG. 5, the present invention may be configured such that only the branch lines provided with the standard gas flow rate controlling mechanisms 33 respectively having low flow rate ranges (e.g., the second and third branch lines) among the plurality of branch lines are connected.

Also, the above-described embodiment is configured such that in the case where the second or third branch line is selected by the line switching mechanism, the control part 6 automatically outputs the open control signal to the on/off valve provided in the exhaust gas line 5; however, the present invention is not limited to this. That is, regardless of which branch line is selected, on the basis of a target flow rate value of a flow rate controlling mechanism provided in a branch line, the control part 6 may control the on/off of the on/off valve.

Further, the above-described is configured to, depending on the flow rate of the standard gas flowing through the standard gas line 3, control the on/off of the on/off valve 51 provided in the exhaust gas line 5; however, regardless of the flow rate, in the case of using standard gas that is easily adsorbable or modifiable, the control part may control the on/off of the on/off valve 51 of the exhaust gas line depending on the standard gas to be used regardless of the standard gas flow rate.

Besides, it should be appreciated that the present invention is not limited to any of the above-described embodiments, but can be variously modified without departing from the scope thereof.

REFERENCE CHARACTERS LIST

100: Standard gas concentration controller system
2: Diluent gas line
23: Diluent gas flow rate controlling mechanism
3: Standard gas line
3a to 3c: Branch line
33: Standard gas flow rate controlling mechanism
35: Line switching mechanism
4: Output gas line
5: Exhaust gas line
51: On/off valve
52: Flow rate control part
6: Control part

The invention claimed is:
1. A gas concentration controller system configured to mix a first gas and a second gas at a predetermined ratio to produce mixed gas having a predetermined concentration, the gas concentration controller system comprising:
a first gas line that is provided with a first gas flow rate controlling mechanism for controlling a flow rate of the first gas;

a second gas line that is provided with a second gas flow rate controlling mechanism for controlling a flow rate of the second gas;

an output gas line that is joined by the first gas line and the second gas line and configured to output the mixed gas having the predetermined concentration;

an exhaust gas line that is connected to an upstream side of the second gas flow rate controlling mechanism in the second gas line and provided with an on/off valve and a flow rate control part configured to flow the second gas in the exhaust gas line; and a control part configured to, depending on the flow rate of the second gas flowing through the second gas line or a type of the second gas, switch on/off the on/off valve provided in the exhaust gas line, while the flow rate of the second gas in the second gas line is being controlled by the second gas flow rate controlling mechanism.

2. The gas concentration controller system according to claim 1, wherein the first gas is diluent gas, and the second gas is standard gas.

3. The gas concentration controller system according to claim 1, wherein the second gas line has: a plurality of branch lines and the second gas flow rate controlling mechanism is one of a plurality of second gas flow rate controlling mechanisms that are respectively provided on each of the plurality of branch lines; and a line switching mechanism configured to select, from the branch lines, a branch line through which the second gas flows, flow rate control ranges of the second gas flow rate control mechanism provided in the respective branch lines are configured to be mutually different, and the exhaust gas line is connected to, among the plurality of branch lines, a branch line that is provided with a second gas flow rate controlling mechanism having a low flow rate range.

4. The gas concentration controller system according to claim 3, wherein in a case where, among the plurality of branch lines, the branch line that is provided with the second gas flow rate controlling mechanism having the low flow rate range is selected, the control part is configured to open the on/off valve provided in the exhaust gas line.

5. A gas concentration controller program used for a gas concentration controller system configured to mix a first gas and a second gas at a predetermined ratio to produce mixed gas having a predetermined concentration and is provided with:

a first gas line that is provided with a first gas flow rate controlling mechanism for controlling a flow rate of the first gas;

a second gas line that is provided with a second gas flow rate controlling mechanism for controlling a flow rate of the second gas;

an output gas line that is joined by the first gas line and the second gas line and configured to output the mixed gas having the predetermined concentration; and an exhaust gas line that is connected to an upstream side of the second gas flow rate controlling mechanism in the second gas line and provided with an on/off valve and a flow rate control part configured to flow the second gas in the exhaust gas line, the program is configured to instruct a computer to fulfill a function as a control part configured to, depending on the flow rate of the second gas flowing through the second gas line or a type of the second gas, switch on/off the on/off valve provided in the exhaust gas line, while the flow rate of the second gas in the second gas line is being controlled by the second gas flow rate controlling mechanism.

6. A gas concentration controller method using a gas concentration controller system configured to mix a first gas and a second gas at a predetermined ratio to produce mixed gas having a predetermined concentration and is provided with:

a first gas line that is provided with a first gas flow rate controlling mechanism for controlling a flow rate of the first gas;

a second gas line that is provided with a second gas flow rate controlling mechanism for controlling a flow rate of the second gas;

an output gas line that is joined by the first gas line and the second gas line and configured to output the mixed gas having the predetermined concentration; and an exhaust gas line that is connected to an upstream side of the second gas flow rate controlling mechanism in the second gas line and provided with an on/off valve and a flow rate control part configured to flow the second gas in the exhaust gas line, the gas concentration controller method, depending on the flow rate of the second gas flowing through the second gas line or a type of the second gas, configured to switch on/off the on/off valve provided in the exhaust gas line, while the flow rate of the second gas in the second gas line is being controlled by the second gas flow rate controlling mechanism.

* * * * *